United States Patent [19]

Takagishi et al.

[11] Patent Number: 4,892,738

[45] Date of Patent: Jan. 9, 1990

[54] SUSTAINED-RELEASE GRANULAR PHARMACEUTICAL PREPARATIONS

[75] Inventors: Yasushi Takagishi, Hyogo; Toshihiro Ogura, Osaka; Kenji Sasaki, Nara; Shunji Nagata, Hyogo, all of Japan

[73] Assignee: Shionogi & Co., Ltd., Osaka, Japan

[21] Appl. No.: 185,354

[22] Filed: Apr. 18, 1988

Related U.S. Application Data

[63] Continuation of Ser. No. 442,916, Nov. 19, 1982, abandoned, which is a continuation of Ser. No. 265,595, May 20, 1982, abandoned.

[30] Foreign Application Priority Data

May 21, 1980 [JP] Japan ................................. 55-68271

[51] Int. Cl.$^4$ .......................... A61K 9/22; A61K 9/26
[52] U.S. Cl. ................................... 424/468; 424/469; 424/470; 424/472; 424/488
[58] Field of Search ................ 424/468, 469, 470, 472, 424/488

[56] References Cited

U.S. PATENT DOCUMENTS

| | | | |
|---|---|---|---|
| 2,793,979 | 5/1957 | Svedres | 424/22 |
| 2,928,769 | 3/1960 | Gaunt | 424/22 |
| 2,928,771 | 3/1960 | Gaunt | 424/22 |
| 3,062,720 | 11/1962 | Costello | 424/22 |
| 3,101,293 | 8/1963 | Gaunt et al. | 424/22 |
| 3,102,845 | 9/1963 | Fennell | 424/22 |
| 3,146,167 | 8/1964 | Lantz et al. | 424/22 |
| 3,148,124 | 9/1964 | Gaunt | 424/22 |
| 3,629,393 | 12/1971 | Nakamoto et al. | 424/22 |
| 3,773,920 | 11/1973 | Nakamoto et al. | 424/19 |
| 4,199,560 | 4/1980 | Gyarmati et al. | 424/19 |
| 4,261,970 | 4/1981 | Ogawa et al. | 424/19 |
| 4,291,016 | 9/1981 | Nougaret | 424/35 |

FOREIGN PATENT DOCUMENTS

| | | |
|---|---|---|
| 2732335 | 2/1978 | Fed. Rep. of Germany . |
| 835532 | 7/1957 | United Kingdom . |
| 1443923 | 7/1976 | United Kingdom . |
| 2057876A | 4/1981 | United Kingdom . |
| 1589982 | 5/1981 | United Kingdom . |

OTHER PUBLICATIONS

McCallister et al, "Diffuse Reflectance...," *J. Pharm. Sci.*, vol. 59, No. 9, pp. 1287-1289 (1970).

Hazler et al (III), Chem. Abstracts 89, 12153c (1978) of Ger. Off. 2,732,335, 02 Feb. 1978.

Aellig et al, Eur. J. Clin. Pharmacol., (1981), 20 [3], 179-183, A Pharmacodynamic and Pharmacokinetic Comparison of Pindolol 20 MG Retard and a Conventional Tablet, abstr. in Chem. Abstr. 95:175720Y (1981).

*Primary Examiner*—Shep K. Rose
*Attorney, Agent, or Firm*—Birch, Stewart, Kolasch & Birch

[57] ABSTRACT

A favorable sustained-releasing property is given to granular preparations by incorporating therein at least one $C_{16}$–$C_{18}$ saturated fatty acid and/or metal salts thereof at a rate of 10–50% of the total weight of the dosage form. The disclosed dosage form releases the active ingredient both in a low pH region of the stomach and in a high pH region of the intestine at an appropriate rate.

8 Claims, 4 Drawing Sheets

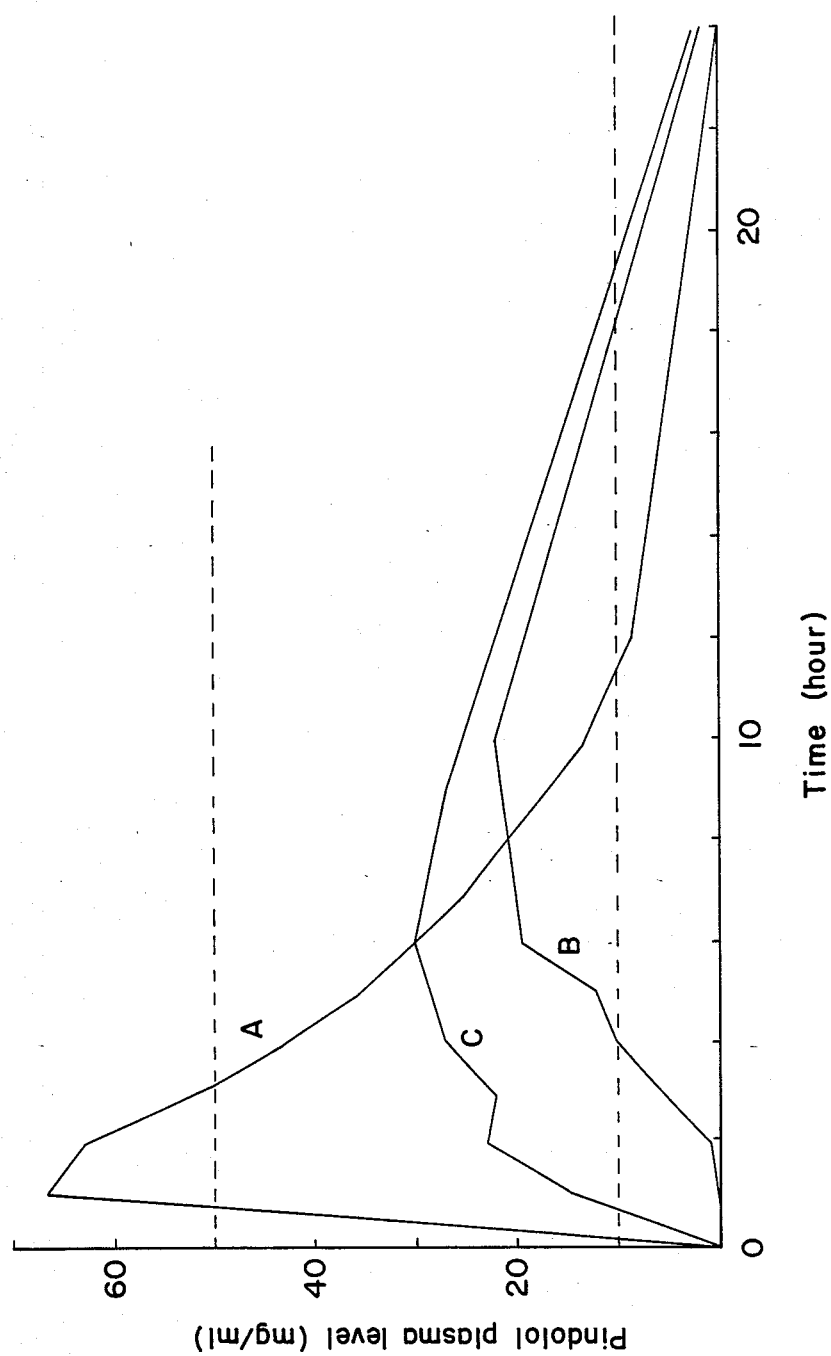

SUSTAINED-RELEASE GRANULAR PHARMACEUTICAL PREPARATIONS

This application is a continuation of application Ser. No. 442,916 filed on Nov. 19, 1982, now abandoned, which is a continuation of copending application Ser. No. 265,595, filed on May 20, 1982, now abandoned.

BACKGROUND AND FIELD OF THE INVENTION

The present invention generally relates to sustained-release pharmaceutical granular preparations. Particularly, it is concerned with such preparations that effectively control the dissolving and/or absorption rates of pharmacologically-active ingredients which are otherwise liable to be decomposed with the gastric juice and/or rapidly absorbed into the living body to raise the concentration in the blood to a dangerous extent.

Certain kinds of pharmacologically active substances, particularly weakly basic ones including their acid addition salts, are rapidly dissolved in the stomach and therefore the blood (serum and/or plasma) levels of the substances are correspondingly rapidly raised.

On the other hand, it is desirable to raise the serum and/or plasma level of a pharmacologically active substance rapidly up to a predetermined level and subsequently maintain the level for a period of time as long as possible.

In the cases of, for instance, antihypertensive agents and hypoglycemic agents, a rapid rise in the serum and/or plasma levels of such agents up to an unexpected degree is a sign of danger for a patient who is given the agent. Accordingly, it is desirable to properly control the rise in the level of the active ingredients.

DESCRIPTION OF THE PRIOR ART

There has hitherto been made a number of proposals for improving a preparation so as to have a satisfactory sustained-releasing property, though only few have actually attained the object of the moderate release of active ingredient in both a low pH region of the stomach and particularly in a high pH region of the upper intestine. The active ingredient must also be protected against the actions of pancreatic enzyme like lypase or esterase for a long period of time to ensure its favorable releasing property.

The proposals in the prior art, however, are still disadvantageous, because some of them require complex formulating procedures such as heat fusion or multiple-layer compression in their manufacturing process and in other cases, the preparations are of dubious reliability and safety in view of, for instance, residual organic solvents used in the manufacturing.

SUMMARY OF THE INVENTION

It is therefore the primary object of the present invention to provide sustained-release granular preparations being free from the above mentioned disadvantages.

It is another object of the present invention to provide preparations demonstrating a satisfactory releasing rate both in a low pH region of the stomach as well as in a high pH region of the intestine.

According to the present invention, there are provided sustained-release granular preparations characterized by incorporating at least one $C_{16}$–$C_{18}$ saturated fatty acid and/or metal salts thereof at a rate of 10–50% by weight of the total weight of the preparation.

The disclosed preparations of course, contain at least one pharmacologically active ingredient, conventional fillers, diluents, stabilizers, and/or binding agents, and other auxiliary agents in addition to said $C_{16}$–$C_{18}$ saturated fatty acid and/or metal salts thereof.

The term "granular preparation", used in this specification and claims, means regular granules, fine granules and beads obtained by a method other than an impact compression molding. Therefore, such particle-like preparations as tablet fragments (obtained by impacting once molded tablets) are excluded from the scope of the present invention.

The term "sustained-release", defined here, means one in which a drug is initially made available to the living body in an amount sufficient to cause the desired pharmacological response as rapidly as is consistent with the properties of the drug determining its intrinsic availability, and one which provides for maintenance of activity at the initial level for a desired number of hours in excess of the activity resulting from the usual single dose of drug.

DETAILED EXPLANATION OF THE INVENTION

As a result of various investigations on a means for attaining the above-mentioned object, the present inventors have now found that it is effective to incorporate a relatively large amount of $C_{16}$–$C_{18}$ saturated fatty acid and/or a salt thereof in the preparation. They have also confirmed the required qualification of the present invention as regards the amount of the added $C_{16}$–$C_{18}$ saturated fatty acid and/or salt thereof as described hereinbelow.

The present invention can advantageously be applied to those pharmacologically-active weakly basic substances or their acid-addition salts. They can be exemplified as arylalkanolamines and aryloxyalkanolamines represented by pindolol, phenothiazines or other three membered ring psychotropic agents represented by chlorpromazine hydrochloride, imidazole derivatives such as metronidazol, and anti-inflammatory agents or sedatives such as quinidine or phenacetin.

The $C_{16}$–$C_{18}$ saturated fatty acid which can be used in the pharmaceutical preparation of the present invention may be a long chain fatty acid containing 16–18 carbon atoms, such as stearic acid or palmitic acid. The metals which form the salts with the $C_{16}$–$C_{18}$ fatty acid may be magnesium, calcium and aluminium. Of these salts, magnesium stearate is the most common and has been contained in tablets molded in an impact compression, as a lubricant, though its content in the tablets is so small that it can never exceed 2% of the total weight of the tablet.

Although there has been a suggestion that magnesium stearate may be used for delaying the disintegration of an oral baccal tablet or troche whose dissolving conditions are completely different from that of ordinary tablets, incorporation of magnesium stearate in a large amount would lead to an incomplete compression. It therefore remains to be only a suggestion and has not yet been actually embodied.

Magnesium stearate has hitherto been used only as a lubricant in an impact tabletting process, but it has never been used in non-impact granules nor in a relatively large amount.

On the other hand, there is one example wherein stearic acid is used in sustained-release tablets molded in an impact compression but the example does not indicate the logical or empirical necessity of incorporating stearic acid into solid dosage forms such as granules, prepared by a method other than impact compression.

As can be seen from the description as regards the preferred embodiments which will be described hereinafter, these $C_{16}$–$C_{18}$ turned fatty acids and/or metal salts thereof give the pharmaceutical preparation a sustained-release property more effective than the heretofore known additives such as fatty oils or waxes e.g., esters (mono- and tri-glyceride) of higher fatty acids, hydrogenated castor oil or carnauba wax.

Of these substances, magnesium stearate (it usually designates a commercially available additive for pharmaceutical preparations and is a mixture of magnesium stearate and magnesium palmitate as its main ingredients) is particularly preferable in view of the fact that it agglomerates very little and is easily pulverizable. These properties permit the preparation of ultra fine particles.

The amount of the $C_{16}$–$C_{18}$ saturated fatty acid and/or metal salts thereof to be added to the granules may preferably be in a range of 10–50 w/w % and more preferably in 15–40 w/w % of the total weight of the granules in order to attain the stated object of the present invention.

If the amount is under 10 w/w %, the advantage due to the addition is not sufficient for attaining the object and an addition which exceeds 50 w/w % can not improve the sustained-releasing property any more, as illustrated in FIG. 4.

This range is, however, not necessarily as absolute one and the amount of addition should of course be adjusted in accordance with the property of the medicament and its behavior in the living body.

On the other hand, a water soluble binding agent which can be used together with this $C_{16}$–$C_{18}$ saturated fatty acid and/or metal salt thereof can be exemplified as methyl cellulose, hydroxypropyl cellulose, polyvinylpyrrolidone, gelatine, starch and hydroxypropylmethyl cellulose.

If the use of an organic solvent (e.g. acetone, ethanol or the like) is permitted, ethyl cellulose or a copolymer of methacrylic acid and methyl methacrylate may be used as a suitable binding agent.

As other additives, common fillers or diluents, such as crystalline cellulose, lactose, starch, mannitol, sorbitol, calcium sulfate and calcium phosphate may also be used. Of these additives, non water-soluble but hydrophilic ones, for instance, crystalline cellulose, are particularly convenient in view of the object of the present invention.

Furthermore, the sustained-release granular preparation of the present invention may be coated with the known enteric-coating substance, such as shellac, cellulose acetate phthalate (CAP), hydroxypropylmethyl cellulose phthalate (HPMCP), a copolymer of 2-methyl-5-vinylpyridine, methyl methacrylate and methacrylic acid (MPM), and a copolymer of methyl methacrylate and methacrylic acid (Eudragit L or S) on the surface of regular granules or fine granules which had previously been obtained by an extrusion of a moistured mass without being compressed as in an impact tabletting process.

The thus obtained preparation starts to release its pharmacologically-active ingredient after being passed through the stomach and the releasing is controled effectively by the added $C_{16}$–$C_{18}$ saturated fatty acid and/or metal salt thereof.

The sustained-release granular preparation of the present invention may of course be combined with a rapidly-dissolving preparation to raise the blood level of the pharmacologically-active ingredient after administration.

The combination may be made by simply admixing both preparations, or alternatively, it may be prepared by covering the surface of the sustained-release preparation with a layer of a rapidly-dissolving preparation including a pharmacologically active ingredient.

Although the ratio of the combination, of course, depends on the property of the active ingredient, it is found that, in the case of pindolol, for instance, 0.25–0.75 part of the rapidly-dissolving component is suitable and more preferably approximately 0.5 part is particularly suitable for one part of the sustained-release component.

As will be made clear in the Preferred Embodiment described later, the $C_{16}$–$C_{18}$ saturated fatty acid and/or metal salts thereof are highly resistant to the catalytic decomposing action of pancreatic enzymes as well as the interface activating action of the bile.

In contrast to this, preparations made by using fatty oils or waxes, such as triglyceride of stearic acid (tristearine), hydrogenated castor oil or carnauba wax, are susceptible to the catalytic decomposing action of the enzymes and the interface activating action of the bile so as to fail in effective control of the dissolution of the pharmacologically-active ingredient.

On the other hand, stearic acid, stable or intact to the enzymatic action which takes place in the living body through the mucosa cells of the small intestine under the influence of bile acid, is unsatisfactory for release control in the intestine, though still effective in the stomach.

By selecting a dosage form of granular preparations, an addition of a large amount of magnesium stearate is made possible to give a stable sustained-release preparation which minimizes the difference in the stomach passage rate among individuals and in the effect of food taken before the administration.

DESCRIPTION OF THE ACCOMPANYING DRAWINGS

FIGS. 1A and 1B are graphs showing the dissolution rate of the active ingredient from the preparations embodying the present invention in contrast to the comparative preparations, FIGS. 2A and 2B are graphs showing blood levels of the pindolol in the apparently healthy volunteers who have taken the preparations of the present invention and comparative preparations, FIG. 3 is a graph showing the dissolution controlling effects of the preparation of the present invention in contrast to those of the comparative preparations, FIG. 4 is a graph showing an influence on the dissolution rate by changing content of magnesium stearate in the preparations of the present invention, and FIG. 5 is a graph showing the dissolution controlling effects of the other embodiments of the present invention.

DESCRIPTION OF THE PREFERRED EMBODIMENT

Figure 1A:
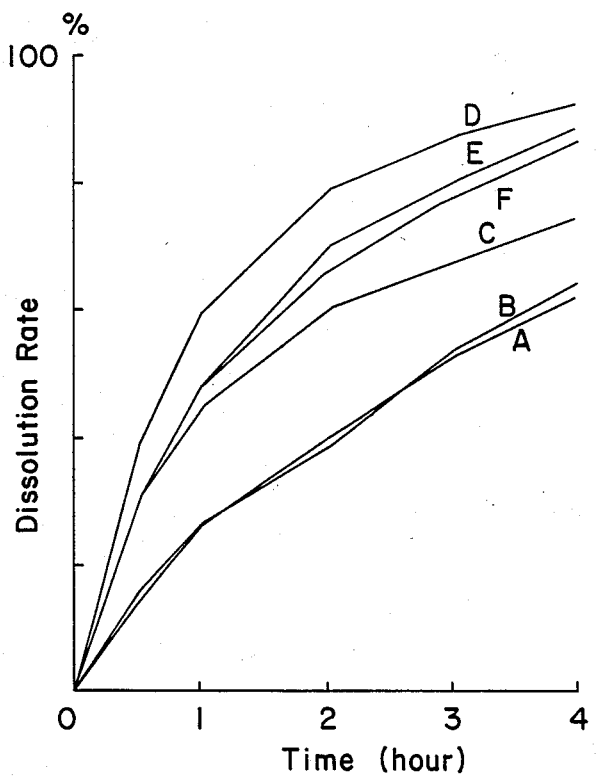

In the following description, the present invention will be elucidated in more detail by referring to the preferred embodiment, wherein each of the examples is described by giving contrast to comparative preparations.

EXAMPLE 1

Granules of Formulations list in Table 1 below are prepared in a conventional method (extrusion of a moistured mass through a screen of 1.0 mm openings).

TABLE 1

| Formulation | (mg per one dose unit) | | | | | |
|---|---|---|---|---|---|---|
| | A | B | C | D | E | F |
| Pindolol | 10 | 10 | 10 | 10 | 10 | 10 |
| Magnesium stearate | 85 | — | — | — | — | — |
| Aluminum stearate | — | 85 | — | — | — | — |
| Stearic acid | — | — | 85 | — | — | — |
| Tristearine | — | — | — | 85 | — | — |
| Carnauba wax | — | — | — | — | 85 | — |
| Hydrogenated castor oil | — | — | — | — | — | 85 |
| Microcrystalline cellulose | 95 | 95 | 95 | 95 | 95 | 95 |
| Methyl cellulose | 10 | 10 | 10 | 10 | 10 | 10 |
| Total | 200 | 200 | 200 | 200 | 200 | 200 |

The thus obtained granules (200 mg, each containing 10 mg of pindolol) are subjected to dissolution tests in compliance with the so called "paddle method". The apparatus 2 defined in [711] dissolution of U.S. Pharmacopeia 20th Ed. (U.S.P.XX) is used for the tests, wherein each 900 ml of the second test fluid defined in Japan Pharmacopeia 9th Ed. under "disintegration test" (a simulated intestinal fluid, and hereinafter will be referred to as "the second JP test fluid" as opposed to "the first JP test fluid", which is a simulated gastric juice, also defined in Japan Pharmacopeia 9th Ed.) and of another second JP test fluid, modified by adding lipase (0.8 mg/ml) therein, are used.

The amounts of pindolol dissolved into the test fluids for one hour and for four hours, during which time the fluid are stirred (100 r.p.m.), are determined by a double wavelength spectrophotometry ($\lambda_1 = 295$ and $\lambda_2 = 287$). The results are summarized in Table 2 below.

TABLE 2

| Formu-lation | Pindolol dissolved (%) for one hour second JP test fluid | (+lipase) | Pindolol dissolved (%) for four hours second JP test fluid | (+lipase) |
|---|---|---|---|---|
| A | 25.2 | 26.7 | 62.2 | 66.7 |
| B | 26.1 | 27.0 | 64.3 | 64.0 |
| C | 44.3 | 38.5 | 75.0 | 68.0 |
| D | 58.8 | 68.6 | 92.5 | 100.0 |
| E | 48.2 | 67.1 | 88.9 | 100.0 |
| F | 47.3 | 69.2 | 87.0 | 100.0 |

Figure 1B:
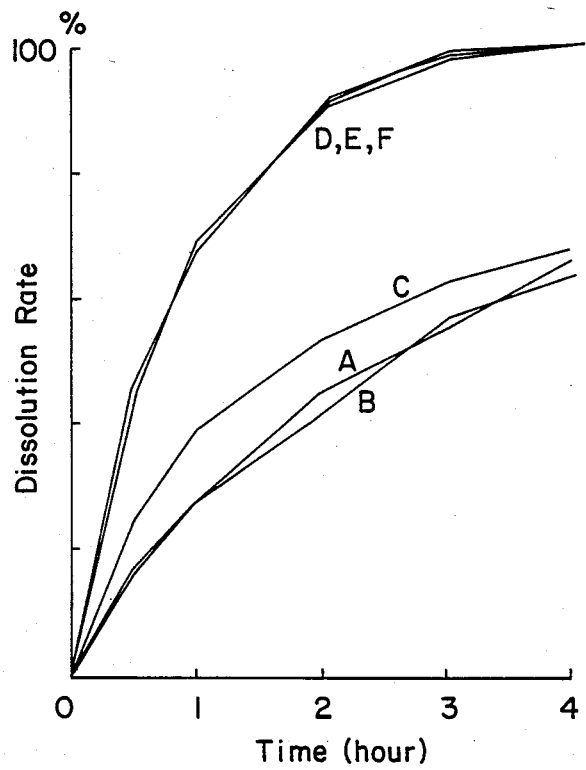

Characteristic curves of the dissolution (FIG. 1A for the second JP test fluid and FIG. 1B for the second JP test fluid plus lipase) over a period of 1-4 hours are also shown.

From the above results, it is found that all of the granules containing tristearine, carnauba wax and hydrogenated castor oil are unsatisfactory in sustained-releasing property in the second JP test fluid and the dissolution is further promoted by the addition of lipase. In contrast to this, both of the granules containing stearic acid and magnesium stearate have a large release delaying effect and are hardly influenced by the enzymatic action of lipase. Stearic acid is, however, very hard to pulverize into to fine particles as compared with magnesium stearate and, thence, the latter is evaluated to be preferable in view of the manufacturing process.

EXAMPLE 2

Granules of Formulation A disclosed in Example 1 are enteric-coated with Eudragit L (available from Rohm Pharma GmbH, Darmstadt, W. Germany) and given to two groups of 4 beagles, one group of which has been fasted overnight and another group being 30 minutes after feeding at a dose of 0.5 mg/kg. The blood level of pindolol is determined from time to time. The results (average value of 4 beagles) are shown in FIG. 2A (solid curve: fasted group and broken curve: fed group).

Figure 2A:
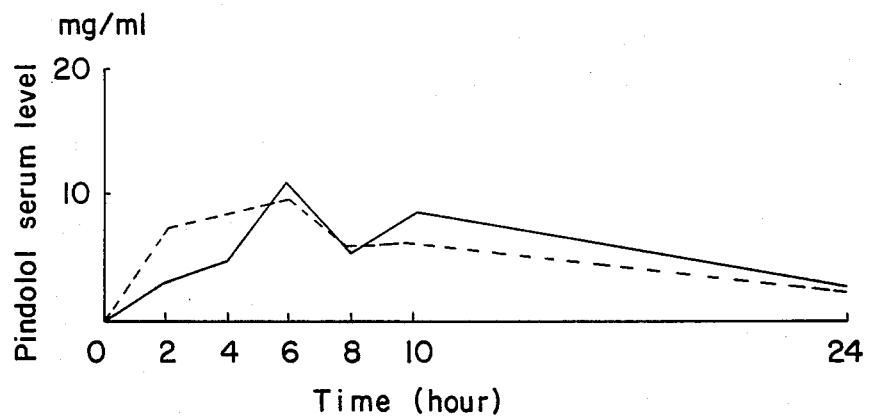
Figure 2B:
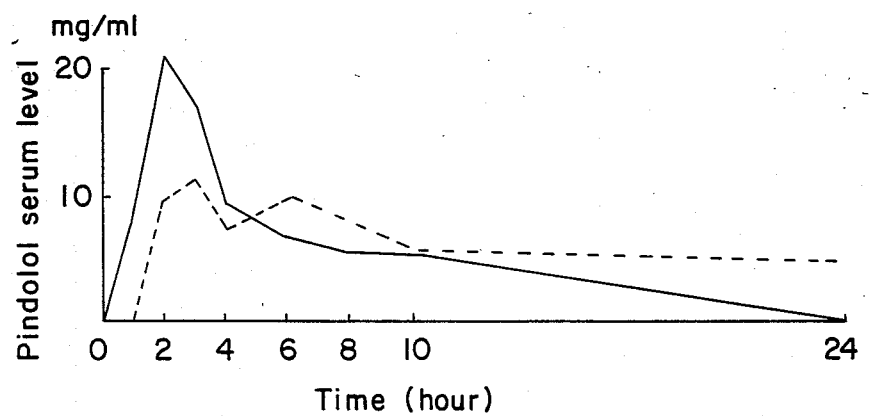

FIG. 2B indicates the results of comparative experiments in which lactose has been used in place of magnesium stearate in preparing the enteric-coated granules (The pindolol level was determined by HPLC).

By comparing the curves in FIG. 2A with those in FIG. 2B, it is found that the food given before the administration has a great influence on a dissolution rate of an ordinary enteric preparation in the stomach. In contrast to this, the enteric preparation embodying the present invention is only slightly affected by the prior feeding and maintain the blood level of pindolol for a long period of time.

EXAMPLE 3

Three kinds of unit dosage forms listed below are prepared, namely;

(1) Rapidly-dissolving granules (containing 15 mg of pindolol for one dose unit) prepared in accordance with a conventional method, (2) Sustained-release granules (10 mg) prepared in accordance with Formulation A of Table 1 in Example 1, and (3) A combined preparation of the granules (2) with rapidly-dissolving granules (5 mg), in (1).

To seven apparently healthy volunteers after a regular meal are administered one of the above three unit dosage forms, and thereafter the blood level of pindolol is determined. The results are represented by the curves A, B and C, respectively in FIG. 3 (Each being depicted based on the mean values of the seven volunteers).

As can be seen from FIG. 3, the characteristic curve A showing the blood level of pindolol obtained with the rapidly dissolving granules (1) exceeds 50 ng/ml level one hour after the administration. The preparation is able to maintain the 10 ng/ml level only for about 10 hours, at which level the preparation shows an acceptable pharmacological effect.

In contrast to this, the sustained-release granules of (2) are insufficient in rise-up characteristics but can maintain the 10 ng/ml level longer as shown by the characteristic curve B. The combined preparation (3) satisfies the both requirements, i.e., the desired rise-up characteristics and the prolonged 10 ng/ml level period, as shown by the curve C.

EXAMPLE 4

Another dissolution experiment similar to those described in Example 1 is performed on the granules prepared in accordance with Formulation A of Example 1, varying the amount of magnesium stearate incorporated therein from 0% to 90% (the content of the crystalline cellulose is therefore varied from 90% to 0%, correspondingly).

Figure 4:
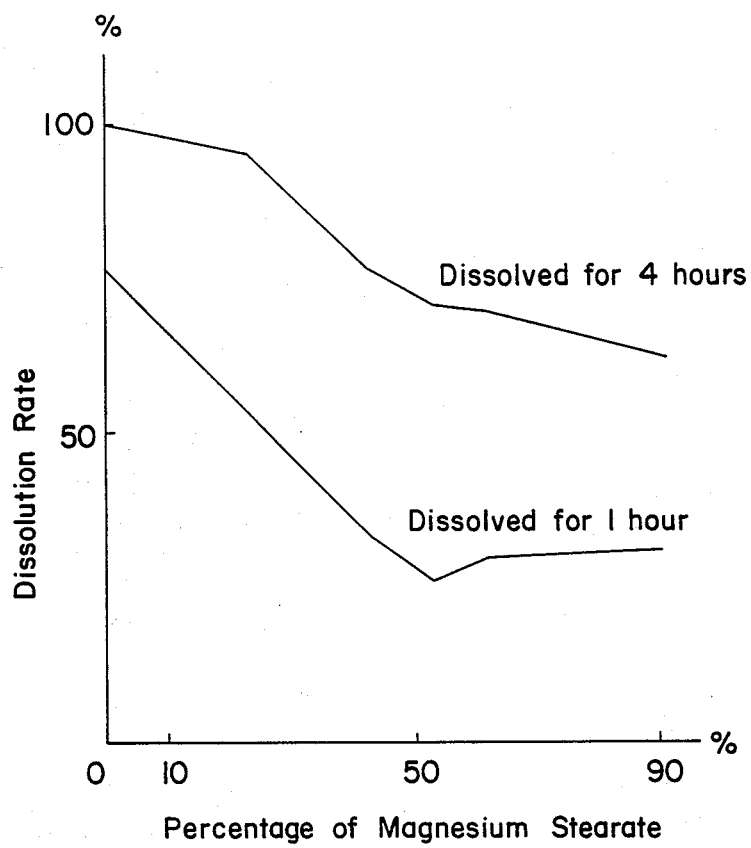

The amounts of pindolol, released from the granules of the respective preparation into the second JP test fluid for one hour and four hours, respectively, are determined in the same manner to give the results shown in FIG. 4.

From the above results, it is confirmed that magnesium stearate delays the releasing time at a content of 10% to 50%.

EXAMPLE 5

Figure 5:
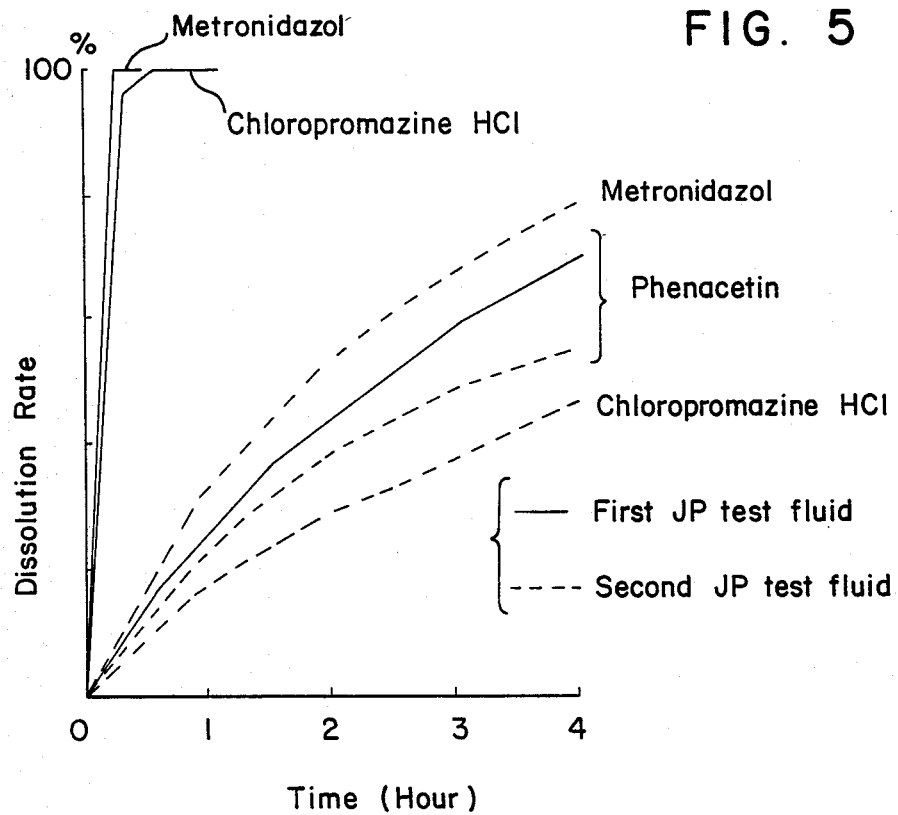

A further dissolution experiment similar to those described in Example 1 is performed on the granules prepared in accordance with Formulation A of Example 1 but containing phenacetin, chlorpromazine hydrochloride or metronidazol as the pharmacologically-active ingredient, in the first JP test fluid and in the second JP test fluid respectively. The releasing rate of the ingredients are determined from time to time. The results are shown in FIG. 5.

From the above results, it is found that the object of effective delay in dissolution can be attained with each of the tested preparations in an enteric form. In the case of phenacetin, the same effect can also be obtained in a non-enteric form.

We claim:

1. A pindolol sustained-release granular preparation comprising an enteric coated sustained-release component prepared by an extrusion of a moistened mass of a mixture which comprises 1–10 wt. % of pindolol, 10–50 wt. % of at least one metal salt of a $C_{16}$–$C_{18}$ saturated fatty acid selected from the group consisting of magnesium stearate, calckium stearate, magnesium palmitate, calcium palmitate, aluminum stearate and aluminum palmitate, 40–55 wt. % of microcrystalline cellulose and 2–20 wt. % of at least one water soluble cellulose derivative wherein said enteric coating material is a member selected from the group consisting of cellulose acetate phthalate, hydroxypropylmethyl cellulose phthalate, a copolymer of 2-methyl-5-vinylpyridine, methyl methacrylate and methacrylic acid, and a copolymer of methyl methacrylate and methacrylic acid.

2. A pindolol sustained-release granular preparation as in claim 1, wherein said enteric coated sustained-release component is combined with a rapidly-dissolving pindolol preparation to form a single dose unit.

3. A pindolol sustained-release granular preparation as in claim 2, wherein the ratio of combining the sustained release preparation to the rapidly-dissolving preparation is from 4:1 to 4:3.

4. A pindolol sustained-release granular preparation as in claim 2, where in said enteric coated sustained-release preparation is coated with a layer of said rapidly-dissolving preparation.

5. A sustained-release granular preparation as in claim 1, wherein said water soluble cellulose derivative is selected from the group consisting of methyl cellulose, hydroxypropyl cellulose and hydroxypropylmethyl cellulose.

6. A sustained-releasing granular preparation as in claim 5, wherein said water soluble cellulose derivative is methyl cellulose.

7. A sustained-release granular preparation as in claim 5, wherein said water soluble cellulose derivative is hydroxypropyl cellulose.

8. A sustained-release granular preparation as in claim 5, wherein said water soluble cellulose derivative is hydroxypropylmethyl cellulose.

* * * * *